United States Patent [19]

Villax et al.

[11] Patent Number: 5,673,686

[45] Date of Patent: Oct. 7, 1997

[54] MEDICAMENT INHALER AND METHOD

[75] Inventors: Peter Villax, Lisbon; Rui Peres, Cascais, both of Portugal; William Richard Treneman, Cambs, Great Britain; Iain Grierson McDerment, Herts, Great Britain; Martin Bunce, London, Great Britain

[73] Assignee: Plurichemie Anstalt, Liechtenstein

[21] Appl. No.: 382,428

[22] Filed: Feb. 2, 1995

[30] Foreign Application Priority Data

Feb. 2, 1994 [PT] Portugal ................... 101450

[51] Int. Cl.$^6$ ........................ A61M 15/08
[52] U.S. Cl. ................ 128/203.15; 128/203.12; 128/203.19; 128/203.21; 128/203.23; 604/58
[58] Field of Search ............... 128/203.12, 203.15, 128/203.19, 203.21, 203.23; 604/58; 131/270, 273

[56] References Cited

U.S. PATENT DOCUMENTS

| 1,827,463 | 10/1931 | Davis | 604/58 |
|---|---|---|---|
| 2,517,482 | 8/1950 | Hall | 128/203.21 |
| 2,549,303 | 4/1951 | Friden | 128/203.15 |
| 2,672,865 | 3/1954 | Wills | 128/203.15 |
| 3,888,253 | 6/1975 | Watt et al. | 128/203.21 |
| 3,949,751 | 4/1976 | Birch et al. | 128/203.15 |
| 3,991,761 | 11/1976 | Cocozza | 128/203.15 |
| 4,013,075 | 3/1977 | Cocozza | 128/203.15 |
| 4,064,878 | 12/1977 | Lundquist | 128/203.15 |
| 4,105,027 | 8/1978 | Lundquist | 128/203.21 |
| 4,116,195 | 9/1978 | James | 128/203.21 |
| 4,192,309 | 3/1980 | Poulsen | 128/203.15 |
| 4,206,758 | 6/1980 | Hallworth et al. | 128/203.21 |
| 4,210,140 | 7/1980 | James et al. | 604/58 |
| 4,265,236 | 5/1981 | Pacella | 128/203.23 |
| 4,338,931 | 7/1982 | Cavazza | 128/203.21 |
| 4,423,724 | 1/1984 | Young | 128/203.21 |
| 4,524,769 | 6/1985 | Wetterlin | 128/203.15 |
| 4,846,168 | 7/1989 | Abiko et al. | 128/203.15 |
| 4,860,740 | 8/1989 | Kirk | 128/203.15 |
| 4,889,114 | 12/1989 | Kladders | 128/203.15 |
| 4,907,583 | 3/1990 | Wetterlin | 128/203.15 |
| 4,995,385 | 2/1991 | Valentini et al. | 128/203.21 |
| 5,042,472 | 8/1991 | Bunin | 128/203.15 |
| 5,048,514 | 9/1991 | Ramella | 128/203.15 |
| 5,152,284 | 10/1992 | Valentini et al. | 128/203.21 |
| 5,239,993 | 8/1993 | Evans | 128/203.15 |
| 5,372,128 | 12/1994 | Haber et al. | 128/203.15 |
| 5,379,763 | 1/1995 | Martin | 128/203.15 |

FOREIGN PATENT DOCUMENTS

| 0404454 | 12/1990 | European Pat. Off. | A61M 15/00 |
|---|---|---|---|
| 573128 | 7/1991 | European Pat. Off. | A61M 15/00 |
| 5814473 | 7/1993 | European Pat. Off. | A61M 15/00 |

(List continued on next page.)

OTHER PUBLICATIONS

"The Fluid Mechanics of Cromolyn Sodium Inhalers Used for Asthma Prevention" by Eugene Niemi, Jr. University of Lowell, MA

*Primary Examiner*—Vincent Millin
*Assistant Examiner*—V. Srivastaya
*Attorney, Agent, or Firm*—Ostrolenk, Faber, Gerb & Soffen, LLP

[57] ABSTRACT

A new inhalation device, which during operation causes an aerosol to be formed inside a chamber such as a capsule (4) which occludes one end (3) of the inhalation tube (1), the capsule having holes at its extremities (7,8) which admit airflow. The airflow causes the powder contained inside the capsule to be surprisingly transported to the capsule extremity contrary to the direction of inhalation, that is towards the air entry holes in the capsule, and then to form an aerosol until all powder has been removed from the capsule or chamber through the tube (1), the during of inhalation being chiefly regulated by the size and proportion of the capsule holes. The tube (1) has air inlets downstream of the capsule to permit a balanced airflow that will transport the finely suspended powder into the lungs, maximizing the fraction of medicament deposited therein.

10 Claims, 2 Drawing Sheets

FOREIGN PATENT DOCUMENTS

| | | | |
|---|---|---|---|
| 7616041 | 5/1976 | France | A61M 15/00 |
| 1047385 | 3/1952 | Germany | 604/58 |
| 1182779 | 9/1966 | United Kingdom | A61M 15/00 |
| 1118341 | 7/1968 | United Kingdom . | |
| 1561835 | 3/1980 | United Kingdom | A61M 15/00 |
| 2178965 | 2/1987 | United Kingdom | A61M 15/00 |
| 2242134 | 9/1991 | United Kingdom | A61M 15/00 |
| 92/09322 | 6/1992 | WIPO | A61M 15/00 |

MEDICAMENT INHALER AND METHOD

BACKGROUND OF THE INVENTION

This invention relates to a method of fluidizing a powdered medicament for inhalation and to a powdered medicament inhaler device.

Pressurized inhalers for administering a metered dose of powdered medicament have long been known, but their use of chlorofluorocarbons as propellants is environmentally undesirable, and there is currently a renewed interest in breath-actuated powder inhalation devices.

There are many known devices for the self-administration of a powdered medicament by inhalation. These devices comprise an inhalation tube through which the patient inhales into his mouth or nose, and means for releasing a dose of powder into the air stream so that it is carried in the air stream through the mouth and throat into the lungs. Some devices contain a store of powder and are arranged to release a metered dose each time the device is used. Others utilize frangible capsules which contain a unit dose of medicament. These devices usually also comprise some means for puncturing or breaking the capsule to release the contents. Examples of capsule-using devices are shown in GB-A-1561835, U.S. Pat. No. 4,889,114 and U.S. Pat. No. 3,991,761.

Some capsule using devices have a low resistance to airflow and, as a result, during operation the powder tends to be administered too quickly and all at once. With the airflow saturated with powder, a considerable quantity of the powder can impinge in the mouth and throat, where it serves no beneficial therapeutic effect; indeed, the chief objective of the device, from a therapeutical aspect, is the maximization of the quantity of powder that reaches the lungs, a concern which until recently had remained secondary.

Whilst many known powder devices have proved reasonably satisfactory in practice, they all have the disadvantage that the user has no simple means of knowing, during use, whether the full dose of medicament has actually been administered. Thus, in the commercially available known devices, the powder dose to be administered is hidden within the device so that at the time of inhalation the user cannot be certain that it has all been released and inhaled. Furthermore, in some known devices there is a visible build-up over a period of use of a powder deposit in the device, requiring frequent cleaning. A further disadvantage of some known powder devices is their mechanical complexity, resulting in an increased production cost and difficult assembly.

We have now devised a method for fluidizing a powdered medicament for inhalation and an inhalation device, which can be simple to operate and therapeutically efficient, and can give the user clear evidence of effective release of capsule contents during the inhalation process.

SUMMARY OF THE INVENTION

According to one aspect of the present invention, there is provided a method of administering a powdered medicament by inhalation, which comprises drawing air through an inhalation tube which is substantially closed by a chamber (e.g. a capsule such as a gelatine capsule) containing the medicament, the chamber having air passage holes to allow air to be drawn therethrough to fluidize and remove the powdered contents therefrom into the tube, and admitting air to the tube downstream of the chamber.

The invention also provides a powdered medicament inhaler which comprises an inhalation tube, chamber receiving means therein whereby a chamber can be received to substantially close the tube, and an air inlet downstream of the chamber receiving means.

The invention further provides a powdered medicament inhaler which comprises an inhalation tube, a chamber substantially closing the tube and an air inlet downstream of the chamber, the chamber having small through holes to permit air flow therethrough into the tube.

In accordance with a feature of the invention, in use of the inhaler the inhalation tube is substantially closed by the chamber. By this, we mean that the normal air flow possible through an open inhalation tube is essentially blocked or prevented by the chamber. The chamber does have some orifices therein to permit air to be drawn through it into the inhalation tube, but these are small in relation to the tube diameter.

In accordance with a further feature of the invention, the inhalation tube, although it is substantially blocked in use by the chamber, has an air inlet to admit air freely to the tube downstream of the chamber (i.e. between the chamber and the mouth end of the inhalation tube). In this way, the user can draw an adequate supply of air through the tube, but only a small part will have come through the chamber. We have found that this simple construction can give excellent fluidization of powder inside the chamber and excellent flow of powder directly through the tube, mouth and throat into the lungs. We have also found that this fluidization is important to provoke the dispersion of powder agglomerates into the desired fine particles.

Furthermore, by careful selection and control of the airflow permitted through the chamber, the device can be turned to suit different users and/or different medicaments.

The chamber for containing the powdered medicament can, for example, be constructed integrally with the tube, or it may be a separate unit receivable or connectable to the tube. The chamber can include a dose providing means for supplying a unit dose of medicament to the chamber ready for inhalation. The chamber can include a dose providing means for supplying a dose unit of medicament to the chamber ready for inhalation. Alternatively, and in accordance with a preferred aspect of this invention, the chamber comprises a capsule which may be conventional apart from the provision therein of holes for the air flow therethrough. The invention will hereafter be described mainly with reference to its use of a capsule chamber but it is to be understood that the invention is not limited to the use of a capsule.

In use of an inhaler of the invention, air is drawn through the capsule or other chamber to fluidize ("aerosolize") the powder therein. The air entry holes in the chamber should be of a size small enough to severely restrict the admission of air into the chamber, when compared to the main airflow created by the user inhaling through the device. This causes a low pressure area inside the chamber in front of the air entry holes, causing the powder to move at first toward that area, from which it is then fluidized and transported in the opposite direction, toward the air exit holes and into the tube. The aerosol so generated is then diluted by admission of air into the inhalation tube, downstream of the chamber via one or more air inlets, so assisting the delivery of the powder to the lungs.

In a very simple and elementary form, the inhaler of the invention comprises a simple tube one end of which is receivable in the user's mouth (or nostril) and the other end of which is sized to receive in friction fit a gelatin or plastic capsule containing the medicament. Between the capsule and the mouth end of the tube, one or more air-inlet holes are provided. The capsule has one or more air passage holes at its outer end, and air/powder passage holes at its inner end to release the powder into the inhalation tube during use of the device. The capsule can be visible during use of the device so that the user can see the aerosolization of the powder therein and be assured as to its substantially complete emptying into the inhalation tube.

It will be appreciated that, unlike certain prior devices where powder capsules have been used, the capsule in the present invention in neither made to rotate, to vibrate or to be twisted open. Here, the only movement present is that of the powder within the capsule, which passes through the inhalation tube to the lungs.

The inhalation tube is provided with one or more air inlets to provide a supply of air into the tube downstream of the chamber. We prefer to provide such inlets close to the end of the chamber. In one construction, the inlet(s) can be around the periphery of the chamber but more usually they will be slightly spaced downstream of the chamber. The size of the air inlet(s) will depend on the overall construction of the device as will be more fully described hereafter.

The inhalation tube itself can be, for example, a straw or the like, or it can be a flexible or rigid plastics or other tube. It can be disposable (for once-only use) or it can be made for continued use, the used capsule shell (or other chamber) being removed after each use. The nature of the tube is not critical except for the provision of the air inlet(s) and for the provision of the capsule-receiving means.

The capsule-receiving means (or, more generally, the chamber receiving means) is arranged so that, when a capsule is located therein, the through-bore of the inhalation tube is blocked by the capsule. The seal need not be perfect and, indeed, in one arrangement described below an air inlet passage is provided between the periphery of the capsule and the tube. However, generally the capsule will be a tight friction fit in the bore of the tube to substantially occlude it. In this way, during use of the device, most of the inhaled air is supplied by the air inlet(s) with only a small quantity being admitted through the capsule holes. In a simple arrangement, the capsule-receiving means is the appropriately dimensioned inside end of the inhalation tube. In other more complex arrangements, the capsule receiving means can be, for example, a separate unit attachable to the inhalation tube as desired.

In one particular aspect of the invention, the powdered medicament inhaler of the present invention is for use with standard (or specially made) conventional-type capsules containing unit doses of medicament, and the invention will hereafter be so described. As stated previously, it is possible, however, to use other forms of chamber for housing unit doses of medicament, and to provide these to the inhalation tube to achieve essentially the same effect as with the capsules, and such arrangements are included herein.

The capsules for use in the inhalers of the invention must be punctured before use so as to allow an air flow therethrough. To achieve this, one or more holes are formed in the capsules. In a preferred arrangement, the holes are formed at each of the ends of the capsule, but other arrangements are possible. When the capsule is located in the capsule-receiving means, one hole or set of holes (the "exit holes") must open into the inhalation tube and the other hole or holes (the "entry holes") must open to an air supply. We have observed that small air entry holes, of a diameter of less than 1 mm, provide for the best swirl of product inside the capsule. With less restricted air entry holes, the powder may exit the capsule in too short a time to be properly diluted by the air entering through the tube inlets, or may even fail completely to be suspended as an aerosol. The exit and entry holes may be of the same or different sizes, and there may be the same or different numbers of each. In general, we prefer that the total area of the exit holes be greater than, for example one half to three times greater than, the total area of the entry holes. However, the optimum arrangement can be determined by routine trial and experiment. Instead of using capsules which have different puncture areas at each end, it is possible to use capsules equally punctured at each end, but to restrict the air supply to the air entry holes of the capsule through the use of a similarly pierced cover or cap fitted over the air entry side of the capsule.

Capsules which have been punctured for use in the present invention are novel per se and form a further aspect of the present invention.

The passage of air through the punctured capsule fluidizes the powder therein, and causes it to be finely suspended. The turbulence is visible through the clear wall of the capsule, and the user simply inhales for as long as powder is visible in the capsule. Because of the restricted admission of air into the capsule, and resulting limited supply out of it, the delivery of powder from the capsule can be kept desirably slow. The slowness of the emptying of the powder is a highly desirable feature of this device, as it permits to match the time it takes to empty the capsule with the time it takes to fill the user's lungs. This causes the powder to be finely dispersed and transported by air flow, reducing the quantity of powder becoming stuck in the user's mouth or throat, and increasing the proportion which reaches the lungs.

In general, most of the air inhaled will enter the inhalation tube via the air inlet(s) therein, the proportion reaching 80%, or more in certain cases. The remainder comes through the capsule and, in so doing, entrains the powder therein. In any particular case, routine trial and experiment will reveal the optimum arrangement for air flows, to achieve the desired effects. One feature which can be achieved in the devices of the invention is a level of resistance to air flow which makes the device comfortable for the user by reducing the effort required to empty the capsule.

The role of air passages in the device is important. In the following description, the capsule holes are assumed to have all the same diameter, so that a variation in the number of holes results in a proportionate and measurable change in their total surface area.

We have found that by having fewer entry holes than exit holes in the capsules, it is possible to slow down the rate at which the powder is drawn out of the capsule. All other things being equal, the fewer the number of air entry holes in the capsule, the slower the release of the powder into the tube and thence through the mouth and into the lungs.

Conversely, by having air inlet(s) on the tube, the total surface area of which can be, for example, 2 to 12 times that of the capsule air entry holes, it is possible to regulate the resistance of the device to the passage of air. All other things being equal, the greater the area of the air inlet(s) on the tube, the greater the quantity of air entering the tube and the greater its powder entrainment capability.

We have also found that by varying the number and combination of air entry and exit holes on the capsule, it is possible to regulate the operation of the device, filled with powders of different particle sizes. Generally, powders with a smaller particle size will require a small total area of entry and exit air holes, than powders with a greater particle size, to achieve the same emptying of the capsule in the same period of time.

Consequently, by experimentally varying the surface area and number of air passages, different embodiments of this invention can be optimized to suit the needs of users with different inhalation abilities, such as children, adults or the elderly, as well as the requirements of powder with different particle sizes and aerodynamic properties.

Thus the existence of various inlets and holes provides for different conditions throughout the device. Within the capsule, the restricted admission of air causes a low pressure area and high air resistance, leading to a fluidization of the powder, finely suspending it. In the tube, the low air resistance caused by more air being drawn through the air inlets results in a more comfortable use to the patient as well as a high powder entrainment capacity. The embodiment of this invention combines the benefits of both low air resistance overall and high air resistance in the capsule, with none of their respective disadvantages.

The provision of holes in the capsules to enable the airflow therethrough can be effected in any suitable way. For examples, needles can be used to form the holes, but we prefer to puncture the capsules with the cutting edge such as a knife blade. In this way, the risk of the puncturing action producing gelatine debris is reduced and control of the size of the cuts enables the airflow to be controlled. Furthermore, we have found that spillage of the powder contents from the capsule can be practically nil when the holes are formed by cutting whereas powder loss can sometimes occur when holes are formed using needles. We have referred above to the use of small entry holes of less than 1 mm. Holes produced by cutting are of an oblong shape, with the cut having a width at its widest point of typically 0.5 mm and a length of 3 to 5 mm.

The device of the invention can include a means for puncturing the pre-filled capsules, and this may form an integral part of the device or it may be a separate unit. Known such devices normally comprise one or more needles arranged to pierce the capsule. A preferred device for use in the present invention would provide a larger area of puncture in one region of the capsule than in another region. Where, in accordance with a preferred feature of the invention, the holes are formed by cutting, cutting blades can be provided to form cuts in, for example, each end of the capsule as desired. In one preferred arrangement, the chamber receiving means comprises a barrel member including an elongate container for housing a single capsule, and knife members are provided to form cuts in each end of the capsule by relative movement between the capsule and the blades.

Alternatively, holes can be pre-formed in the capsules, the holes being temporarily covered to prevent premature loss of powder therefrom. When it is desired to use a capsule, the temporary cover (e.g. adhesive film) can be removed. In one particular embodiment, a capsule (or capsule-like chamber) is provided at one end of an inhalation tube, the outer holes of the capsule being temporarily covered with peelable film and the inner holes also temporarily covered. Then, immediately prior to use, the covers are removed.

In the preferred devices of the invention, where a capsule containing a unit dose is used, there is no shaking or vibration required to empty the contents. This contrast with many prior art devices. In the present invention, the powder is removed by the unique air flow arrangements in the device. In operation the powder contents of a capsule form a "dancing cloud" as they are air-borne. The capsule itself remains substantially motionless during inhalation. In other words, the capsule is stationarily mounted or held in the tube due to its above-noted friction fit mounting in the tube. Expressed differently, the capsule is immovably held relative to the inhalation tube.

Other features and advantages of the present invention will become apparent from the following description of the invention which refers to the accompanying drawings.

BRIEF DESCRIPTION OF THE DRAWING(S)

DETAILED DESCRIPTION OF EMBODIMENTS OF THE INVENTION

Figure 1:
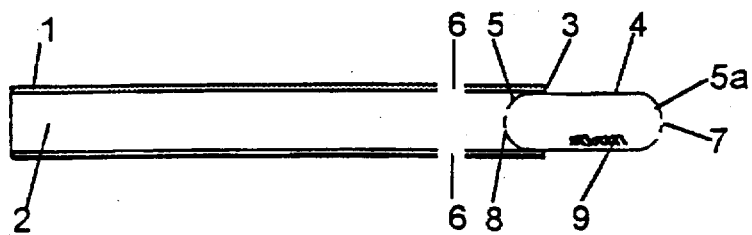
FIG. 1 is a longitudinal section of a first embodiment of the device of the invention.

Referring to the drawings, in which like numerals indicate like parts, there is shown an inhalation tube 1, having an end 2 to be received in the user's mouth, and a remote end 3.

In FIG. 1, a gelatin capsule 4 is snugly fitting and held in remote end 3 of the tube 1. Near the inner end 5 of capsule 4 are two air-inlet orifices 6 in the tube 1.

Figure 4:
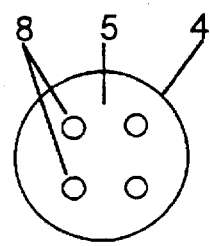
FIG. 4 is a front elevation of an embodiment of the capsule.
Figure 5:
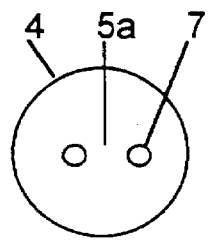
FIG. 5 is a rear elevation of the capsule of FIG. 4.

Capsule 4 is a conventional capsule of two parts with rounded ends 5 and 5a. Outer end 5a has two holes 7 therein and inner end 5 has four holes 8 therein. (See also FIGS. 4 and 5). The holes are the same size (although they need not be). For a standard no. 4 capsule (14 mm×5 mm), the hole size can be 0.65 mm diameter for example. The capsule 4 contains a dose 9 of medicament, either pure or mixed in a carrier powder. The powder should preferably not fill more than about 10% of the volume of the capsule, to provide adequate space for aerosolization of the powder during use.

Figure 2:
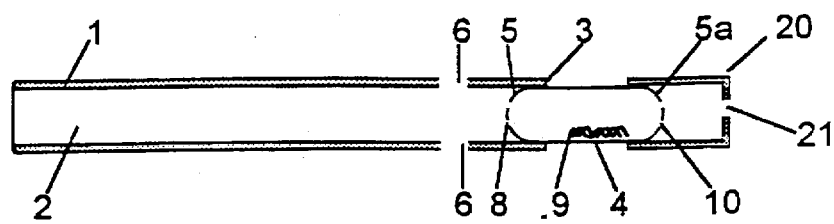
FIG. 2 is a longitudinal section of a second embodiment of the device of the invention.

FIG. 2 differs from FIG. 1 in that a cover 20 is provided over the outer end 5a of capsule 4, which end may have the same number of holes 10 therein as inner end 5. Cover 20 has a restricted air orifice 21.

Figure 3:
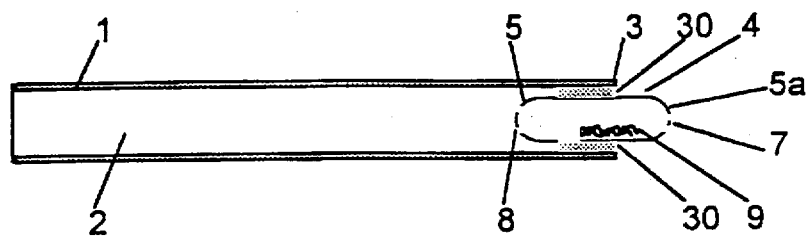
FIG. 3 is a longitudinal section of a third embodiment of the device of the invention.

FIG. 3 differs from FIG. 1 in that air inlets 6 have been omitted and, instead, inner radial fins 30 are provided at end 3 of tube 1 to hold the capsule 4 spaced from the inner wall of the tube and so provide an air inlet passages between the periphery of the capsule 4 and the tube 1.

Figure 6:
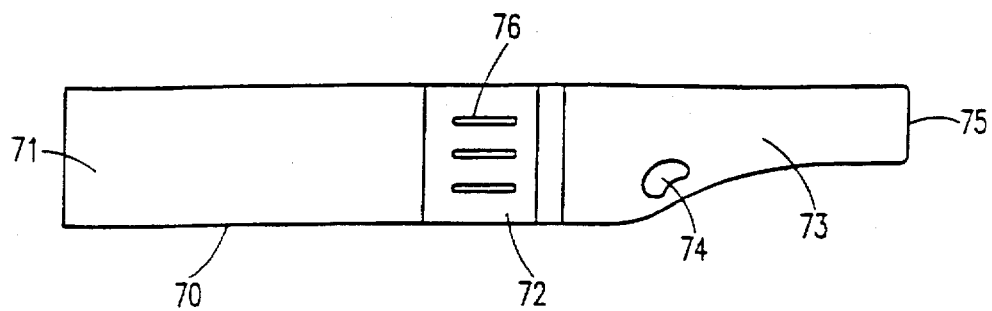
FIG. 6 is a side elevation of a third embodiment of a device of the invention.
Figure 7:
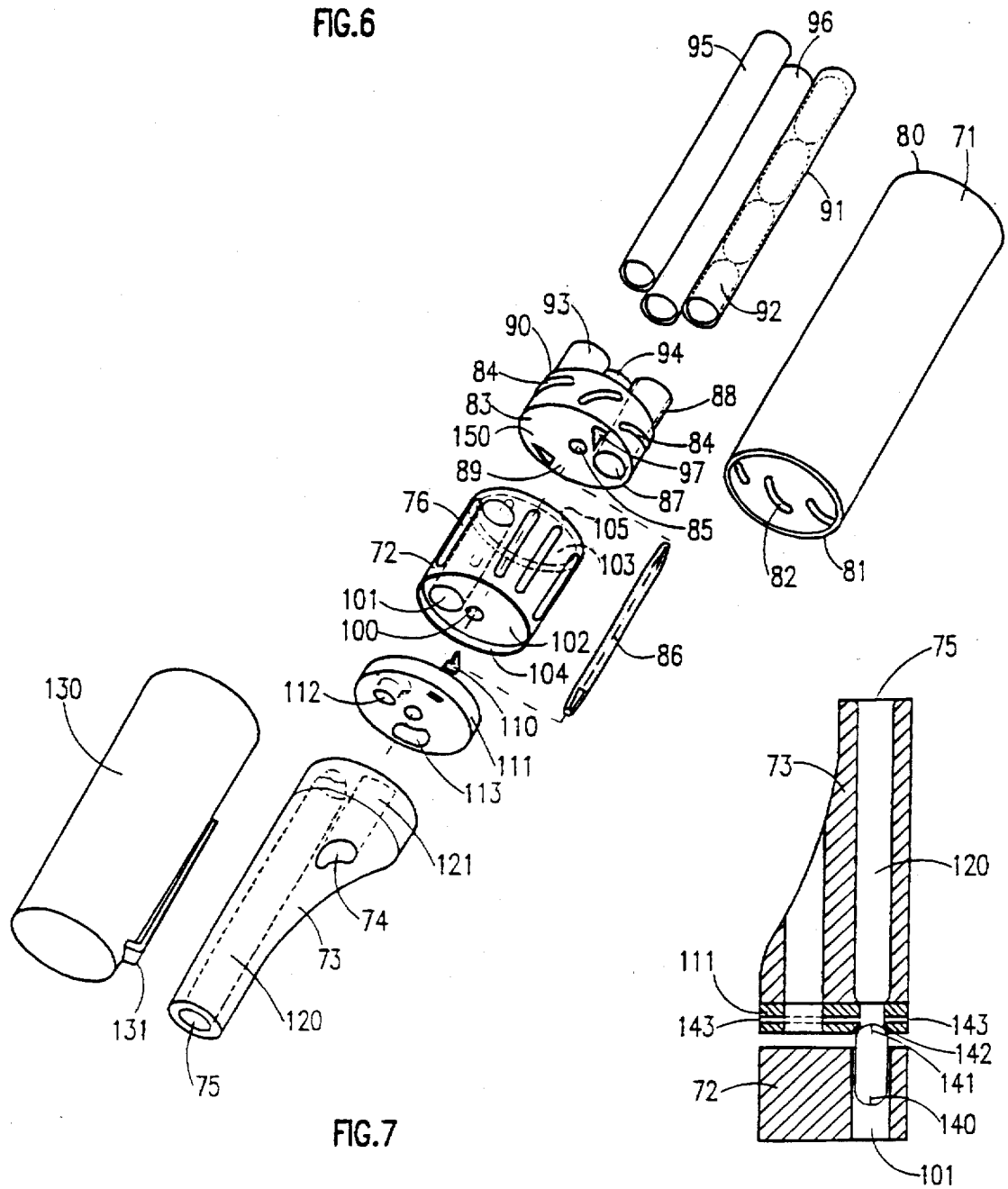
FIG. 7 is an "exploded" view of the components of the device of FIG. 6 (also with a cap)
Figure 8:
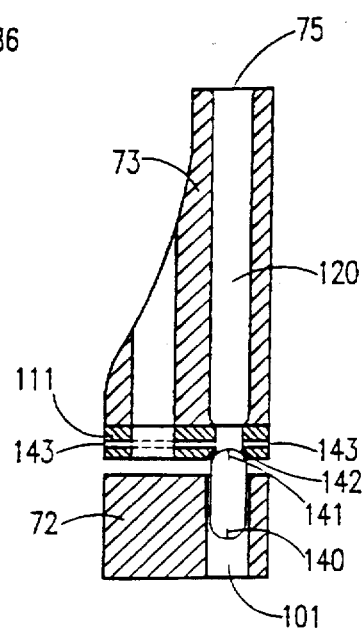
FIG. 8 is a detail section along the axis of bore 120, showing a capsule positioned in the device of FIG. 7, ready for inhalation.

FIGS. 6 to 8 illustrate a third embodiment of inhaler of the invention. In these Figures, like numerals indicate like parts.

FIG. 6 shows the inhaler 70 comprising a capsule reservoir cap 71, a rotatable barrel member 72 and mouthpiece member 73. Mouthpiece member 73 includes a capsule ejection orifice 74 and an inhalation orifice 75. Barrel member 72 includes a series of external ribs 76 for improved manual grip.

FIG. 7 is an "exploded" view of the inhaler of FIG. 6 showing its components. Capsule reservoir cap 71 comprises a cylindrical cap member closed at one end 80, the other end 81 being open and containing internally thereof short screw-threads 82. Reservoir support body 83 is of circular cross-section and includes a series of short screw-threads 84 on the periphery thereof for mating engagement with threads 82 on reservoir cap 71. Support body 83 is formed on its forward face 89 with an axial hole 85 keyed to receive one end of axle 86. Offset from axial hole 85 is a through-bore 87 opening in an upstanding cylindrical sleeve on rear face 90. Receivable in sleeve 88 is a cylinder 91 having a supply of capsules 92, stacked endwise.

Support member 83 also has two other upstanding cylindrical sleeves 93, 94 on its rear face 90, which receive and close the ends of spare capsule supply cylinders 95, 96. Mounted on front face 89 of support 83 is a cutting blade 97 projecting perpendicular to the face 89. Also on face 89 is an ejector ramp projection 150.

Barrel member 72 has an axial bore 100 in which is received axle 86 about which barrel member 72 is rotatable. Barrel 72 has an offset through-bore 101 which constitutes a container for receiving a capsule in use of the device. Around the periphery of cylindrical barrel 72 are external ribs 76. Each end face 102, 103 of the barrel has a peripheral upstanding wall 104, 105 of a height slightly greater than the projecting length of blades 97, 110 so that the blades do not engage the respective ends faces 102, 103 of the barrel member.

Blade support member 111 is of a circular shape and has an axial bore keyed to one end of the axle 86. The member 111 has a first through bore 112 and a second through bore 113. Projecting from member 111 towards barrel member 72 is a knife 110. Member 111 has two air inlets (not shown in FIG. 7; see FIG. 8), which are straight bores perpendicular to the axis of first through bore 112.

Mouthpiece 73 is joined face to face to support member 111. Mouthpiece 73 has a first through bore 120 which constitutes an inhalation tube terminating at inhalation orifice 75 and a second through bore 121 which is a used capsule ejection bore, and terminates at capsule ejection orifice 74. A cap 130 can be provided to cover the mouthpiece 73 when the device is not in use, the cap including a pocket clip 131.

The assembly and operation of the device are as follows. Cylinder 91 containing a supply of powder containing capsules 92 is located in sleeve 88 and a capsule moves under gravity into bore 87 of body 83. Barrel 72 is rotated with respect to supports 83 and 111, about axle 86, to bring bore 101 into line with bore 87. The capsule enters and is fully received into the barrel member. The capsule is slightly longer than the distance between the end faces 102, 103 of the barrel member, as a result of which the opposed ends of the capsule project beyond the said end faces 102, 103.

The barrel has a ratchet (or other device) associated therewith whereby it can be rotated about axle 86 in one direction only and in stepwise motion. The ratchet is not shown. The barrel is now rotated and this brings each projecting end of the capsule, in turn, into engagement with a respective knife member 97, 110. The ends of the capsule are thus slit (see slits 140, 141 in FIG. 8).

The barrel is now advanced further, to bring the capsule into alignment with bore 112 of support 111. The unit is now ready for inhalation. The user inserts the end of the mouthpiece 73 into his/her mouth and inhales. Air is drawn through inhalation tube 120 and bore 112 and thus through bore 101 in barrel 72. The suction draws the capsule forward to enter bore 112 and engage closely the end of bore 120 (see FIG. 8). To facilitate seating of the end of the capsule in bore 120, the end of the bore can be flared at 142 (FIG. 8).

The air flowing through the mouthpiece enters the device primarily through the path of least resistance, which is through air inlets 143 but also, in a smaller amount, through the slits in the capsule. Thus air is drawn through the capsule entering at slit 140 and exiting with the entrained powder at slit 141, for passage via bore 112, where a considerable amount of air is admitted through inlets 143. The air flow entraining the powder now enters bore 120 of the mouthpiece for passage into the user's mouth. As barrel 72 is transparent, the user can repeat the inhalation operation for as long as powder remains visible inside the capsule.

Finally, after the contents of the capsule have been inhaled and the suction has stopped, the empty capsule falls away from the flared end of bore 120 into the barrel bore 101. The barrel then continues to be rotated in the same direction as before to bring the capsule, still in bore 101 into line with the ejection bore 113. Simultaneously, the rearward end of the capsule is engaged by ejector ramp projection 150 which pushes the spent capsule out of ejection orifice 74. Barrel 72 is now rotated to bring the empty bore 101 into registry with bore 87 to receive another capsule from reservoir cylinder 91. When the cylinder is empty, cap 71 is removed and tube 91 is replaced by one of cylinders 95, 96.

The device of FIG. 7 relies on gravity for loading and ejecting capsules; therefore these operations have to be conducted with the device held close to the vertical. The operations of cutting the capsule and inhaling it can be done with the device held in any position.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A powder medicament inhaler, comprising:
    an inhalation tube having a first, downstream end for a person to draw air therethrough and a second, upstream end;
    a medicament holder for holding a quantity of medicament in the form of a fine powder;
    a holding chamber defined in the inhalation tube upstream of the first end for stationarily holding therein said medicament holder relative to said inhalation tube during inhalation;
    an air inlet in the inhalation tube for admitting a first flow of air in response to the suction of a person inhaling through the first end of the inhalation tube; and
    means for drawing a second flow of air through said medicament holder and fluidizing said powder within said medicament holder in response to the suction of a person inhaling through the first end of the inhalation tube, said means including at least one air entry hole and at least one air exit hole in the medicament holder, the area of the air entry hole or holes being substantially smaller than the area of said air exit hole or holes so as to cause the powder to fluidize inside the medicament holder;
    wherein the total area of said air entry holes and air exit holes is configured such that said second flow of air comprises no more than about 20% of the air passing through said inhaler.

2. The medicament inhaler of claim 1, wherein said medicament holder comprises a capsule and wherein said inhaler includes a reservoir for containing a supply of said capsules, and means for supplying a capsule from said reservoir to said holding chamber.

3. The medicament inhaler of claim 2, which further comprises knife means and means for moving said capsule relative to said knife means to form said at least one air entry hole and said at least one air exit hole in said capsule.

4. The medicament inhaler of claim 1, wherein said medicament holder comprises a capsule.

5. The medicament inhaler of claim 4, wherein said at least one entry hole and said at least one exit hole comprise a plurality of small holes at two extremities of said capsule and the small holes are so dimensioned or shaped that admission of air into the capsule is severely restricted.

6. The medicament inhaler of claim 4, wherein one end of the capsule is located in close contact with the second end of the inhalation tube by the force of the suction of the person inhaling through the tube.

7. The medicament inhaler claim 4, wherein during use the movement of the powder in the capsule in visible to the user through the capsule wall.

8. An inhaler according to claim 4, wherein the holding chamber comprises the remote second end of the inhalation tube internally dimensioned to receive the capsule in close friction fit.

9. The medicament inhaler of claim 1, wherein said medicament holder comprises a medicament chamber defined in said inhalation tube adjacent said second end.

10. A method of administering a fluidized powder medicament to a person through inhalation, said method comprising:

providing an inhalation tube having a first, downstream end for the person to draw air therethrough and a second remote, upstream end;

providing a medicament holder for holding a quantity of medicament, the medicament holder having at least one air entry hole defining an air entry hole size and at least one air exit hole defining an air exit hole size, the air entry hole size being substantially smaller than the air exit hole size so as to cause the powder to fluidize inside the medicament holder when air enters through the at least one air entry hole and exits through the at least one air exit hole;

providing a holding chamber defined in the inhalation tube upstream of the first end and immovably holding therein said medicament holder relative to said inhalation tube;

providing an air passage in the inhalation tube and creating a flow of air from said air passage to said first downstream end through suction of the person inhaling through the first end of the tube;

fluidizing the medicament while the medicament is still located inside said medicament holder; and delivering said fluidized medicament from inside said medicament holder into a portion of the inhalation tube located downstream of said medicament holder and carrying the fluidized medicament by the air flowing from the air passage into the body of the person inhaling through the tube.

* * * * *